United States Patent [19]
Kaib

[11] Patent Number: 5,944,669
[45] Date of Patent: Aug. 31, 1999

[54] APPARATUS AND METHOD FOR SENSING CARDIAC FUNCTION

[75] Inventor: Thomas E. Kaib, Westmoreland County, Pa.

[73] Assignee: Lifecor, Inc., Pittsburgh, Pa.

[21] Appl. No.: 08/974,954

[22] Filed: Nov. 20, 1997

[51] Int. Cl.[6] .................................................. X61B 5/00
[52] U.S. Cl. ........................ 600/512; 600/389; 600/515
[58] Field of Search ................................... 600/388, 389, 600/390, 512, 515

[56] References Cited

U.S. PATENT DOCUMENTS

| | | | |
|---|---|---|---|
| 3,534,727 | 10/1970 | Roman | 600/389 |
| 4,136,690 | 1/1979 | Anderson et al. | 600/512 |
| 4,422,459 | 12/1983 | Simson | 128/702 |
| 4,458,691 | 7/1984 | Netravali | 128/705 |
| 4,928,690 | 5/1990 | Heilman et al. | 128/421 |
| 5,000,189 | 3/1991 | Throne et al. | 600/515 |

*Primary Examiner*—William E. Kamm
*Attorney, Agent, or Firm*—Buchanan Ingersoll, P.C.

[57] ABSTRACT

An apparatus and method for sensing cardiac function in a patient, particularly adaptable to being worn by an ambulatory patient. Including sensor to receive ECG signals in at least plane of the patient chest area, and an analyzer to derive a signal representation of the electrical axis of the patient heart. Changes in the signal representation can be evaluated to include heart condition. The axis analyzer and other ECG information can be used to generate rate information used in conjunction with the heart axis signal representation. Incidence of phase zero-crossing of the heart axis signal representation and the magnitude peaks can be used to indicate and distinguish various heart conditions.

36 Claims, 12 Drawing Sheets

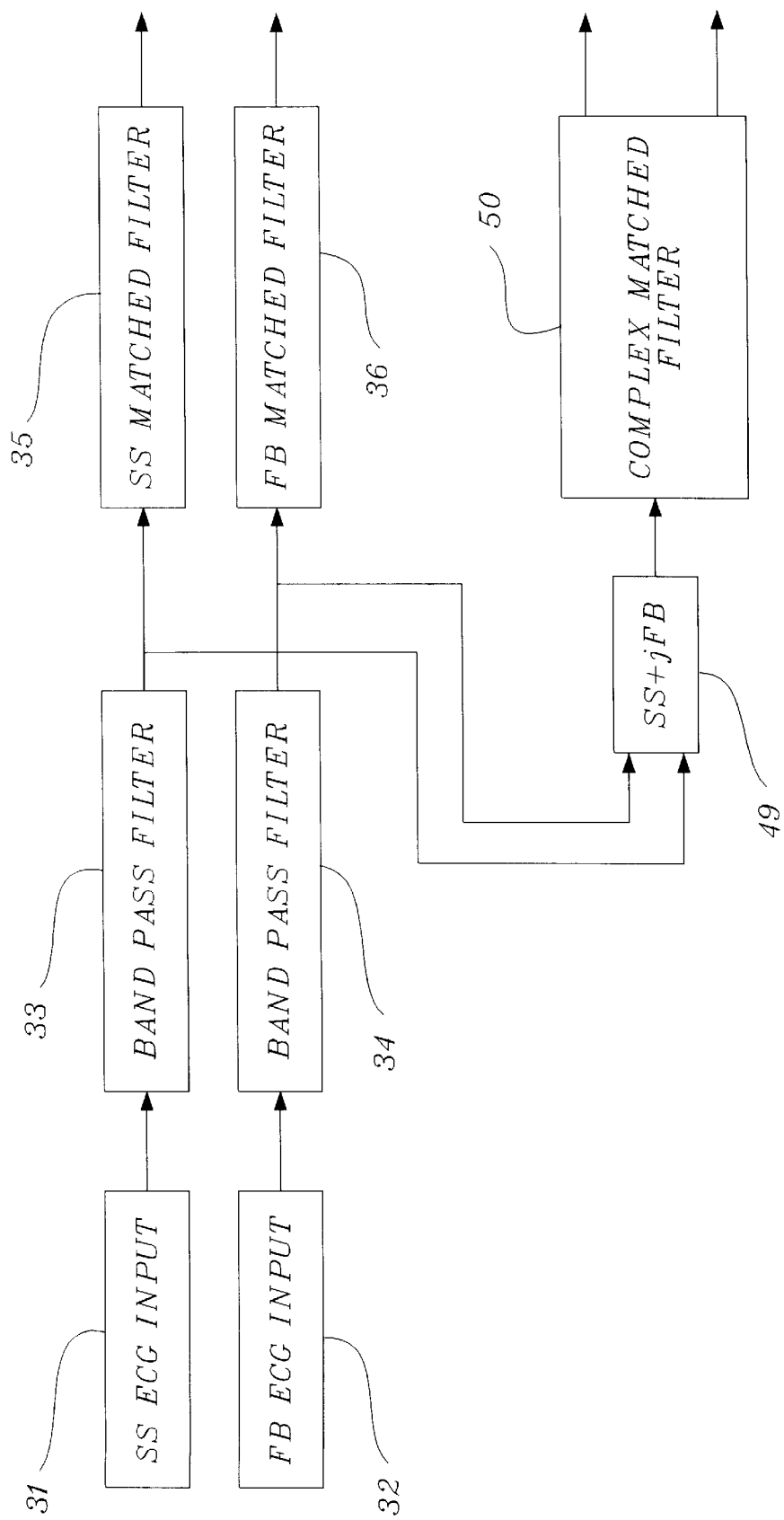

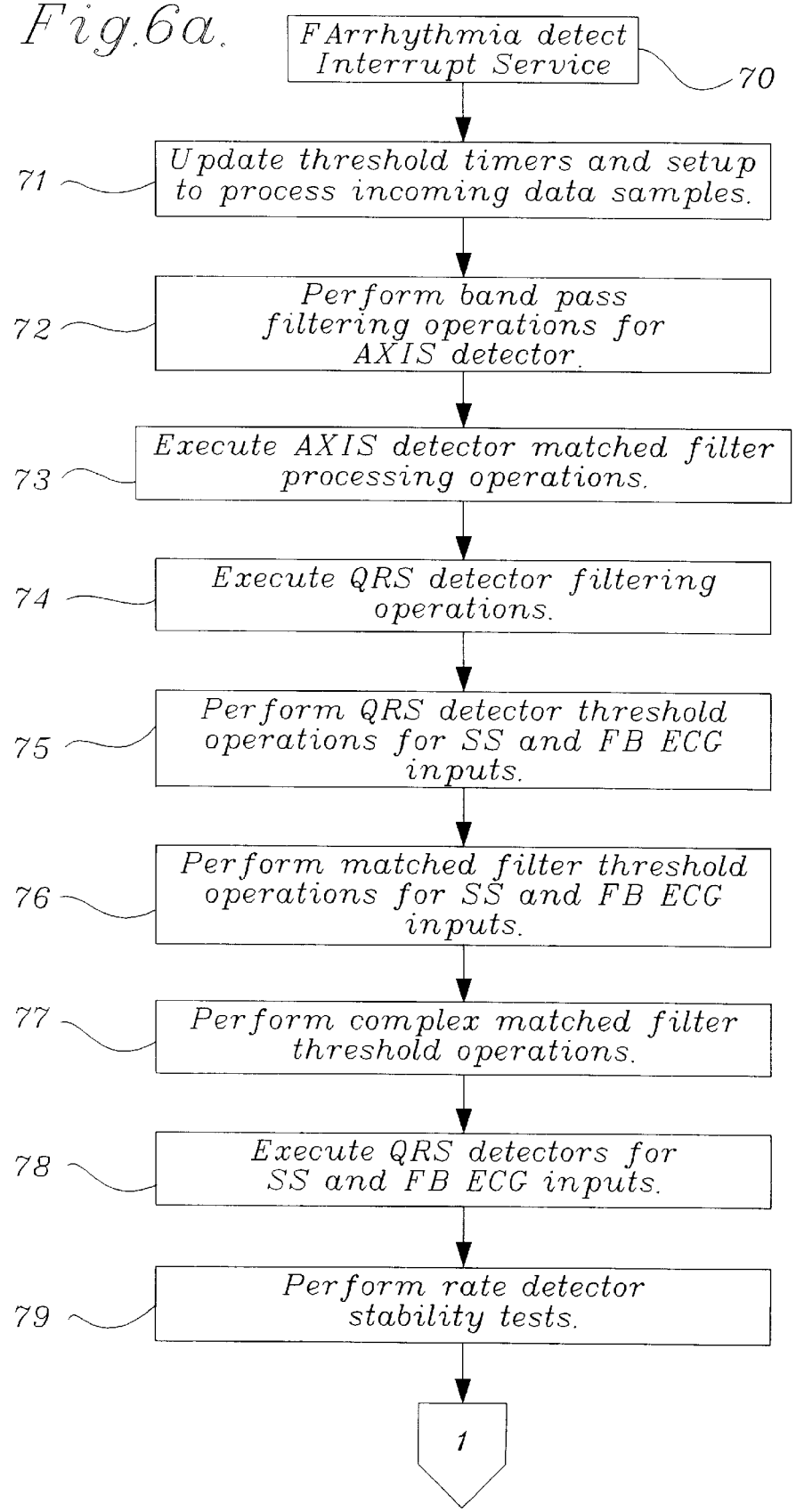

APPARATUS AND METHOD FOR SENSING CARDIAC FUNCTION

FIELD OF THE INVENTION

This invention relates to the detection of cardiac function through the utilization of electrical signals. The detection of abnormal functioning can be utilized to institute treatment. The device and the methods are particularly adaptable to utilization by an ambulatory patient.

BACKGROUND OF THE INVENTION

Many cardiac patients have conditions which can periodically result in excessively fast or erratic heartbeats. If not treated promptly, ventricular fibrillation or certain ventricular tachycardias can result in a fatal outcome. If such tachycardias are promptly detected and treated, such as by electric shock defibrillation, the result of such an attack can often be minimized. Such treatment is normally needed within a few minutes of the onset of the condition to be effective. Therefore, it can be critical to accurately detect such a condition as soon as possible after its occurrence.

In hospitalized patients, the availability of detection equipment and trained medical staff provides a high degree of early detection and treatment. However, persons who are susceptible to such life threatening conditions cannot be hospitalized constantly. It is desirable to have a detection and treatment device which can be utilized by patients especially those that are ambulatory and are not in a hospital setting. Once such device is shown in U.S. Pat. No. 4,929,690. That device incorporates both a detection and treatment mechanism that can be utilized by a non-hospitalized patient. The utilization of such a patient-worn device permits the person susceptible to tachycardia to participate in a relatively normal lifestyle while wearing a device that is comfortable and effective in treating a potentially dangerous arrhythmia condition.

Systems for detection of life threatening tachycardia may utilize electrical sensors to process ECG waveforms and detect QRS signals such as shown in the U.S. Pat. No. 4,928,690. Morphology of QRS signals, or the patient's heart rate may be utilized to determine potentially dangerous conditions. In addition, the change of the patient's heart rate may also be monitored. The patient heart rate or the change of heart rate, coupled with monitoring for a change in QRS morphology, can trigger a preset level to indicate a treatable condition.

Patient cardiac condition can also be indicated by analysis of the QRS signals. These prior QRS analysis system include monitoring of frequency and time based components of the waveform. U.S. Pat. Nos. 4,422,459 and 4,458,691 address frequency components indicative of certain cardiac conditions. U.S. Pat. No. 4,458,691 specifically address the utilization of segmentation of ECG signals, particularly high frequency components with an adaptive filter.

Ventricular tachycardia and ventricular fibrillation are two heart rhythms that are treatable by an electrical shock properly applied to the body of the patient. Both of these conditions occur along with a detectable high heart rate in the patient. Utilization of a threshold heart rate will detect these two conditions in many cases and treatment can begin. Unfortunately, other conditions such as, for example, supraventricular tachycardia also have a high heart rate and these are not treatable by electric shock therapy. Therefore, utilizing a detection methodology which relics only on heart rate to institute treatment may cause treatment to be rendered under conditions where shock therapy may be inappropriate. Therefore, it is desirable to have a method and apparatus which could detect treatable conditions and discriminate in situations such as supraventricular tachycardias which do not require shock treatment. Because it is desired to have such detection systems in situations where human medical assistance may not be available in a timely manner, it is also desirable that such apparatus and method be readily adaptable to patient-worn devices for use by ambulatory patients. Ambulatory patient-worn devices inherently have additional problems in that the patient is generally unrestricted in his movement and detection electrodes may not be able to maintain continuous conductivity. Therefore, it is desirable that detection systems be adaptable to function in a multiple logic decision making topography.

SUMMARY OF THE INVENTION

The apparatus for sensing cardiac function includes sensors that are attached to the patient to sense ECG signals in more than one location about such patient. An axis analyzer is used to derive a signal representation of the electrical axis of the heart of such patient from the ECG signals received from the sensors. Changes in the signal representation of the electrical axis of the heart are evaluated for determining when a treatable condition exists. The signal representation can include a magnitude and a phase component, and in preferred embodiments the phase component includes a zero-cross indication. In some embodiments the analyzer can utilize a complex matched filter to analyze the ECG signals. Treatable conditions can be determined from changes in the heart axis information from a patient normal condition. Specific comparisons of the incidence of zero phase crossing with the periods of peaks of the magnitude component of the heart axis representation can be used to indicate a treatable condition. Logic determining treatable condition can utilize a digital signal processor with other QRS information. Both rate, rate stability and high rate onset can be utilized with the heart axis information to determine treatable conditions. Output from a spectrum analyzer can also be used by the decision logic to verify or indicate a treatable condition. In addition to the comparison of zero phase crossing and the periods of peaks of magnitude in the heart cross representation, the axis analyzer can also provide rate, high rate onset and rate stability information to determine treatable conditions or verify other treatable condition indicators.

The sensors are preferably attached to the patient in two pairs, a front-to-back pair and a side-to-side pair. In some embodiments it is desirable that the signals from the sensors permit analysis in at least one plane that are generally perpendicular to the vertical axis of the heart. Electrodes can also be matrixed by using three electrodes to provide two signals for use which will be out of phase due to the electrode locations.

The apparatus for sensing cardiac function is particularly adaptable to a patient worn device in which a plurality of indicators are analyzed in conjunction to provide a high level of reliability to the treatment decision logic. Other information may include QRS detectors providing side-to-side rates, front-to-back rates, rate stability and high rate onset. Additional input may be obtained from spectral analysis of the ECG signals to provide both a spectral rate and a spectral density indicator.

BRIEF DESCRIPTION OF FIGURES

FIGS. 3a–3c are diagrammatics of an axis analyzer/detector.

FIGS. 6a and 6b are flow charts of an arrhythmia detection algorithm.

DETAILED DESCRIPTION OF FIGURES

Figure 1A:
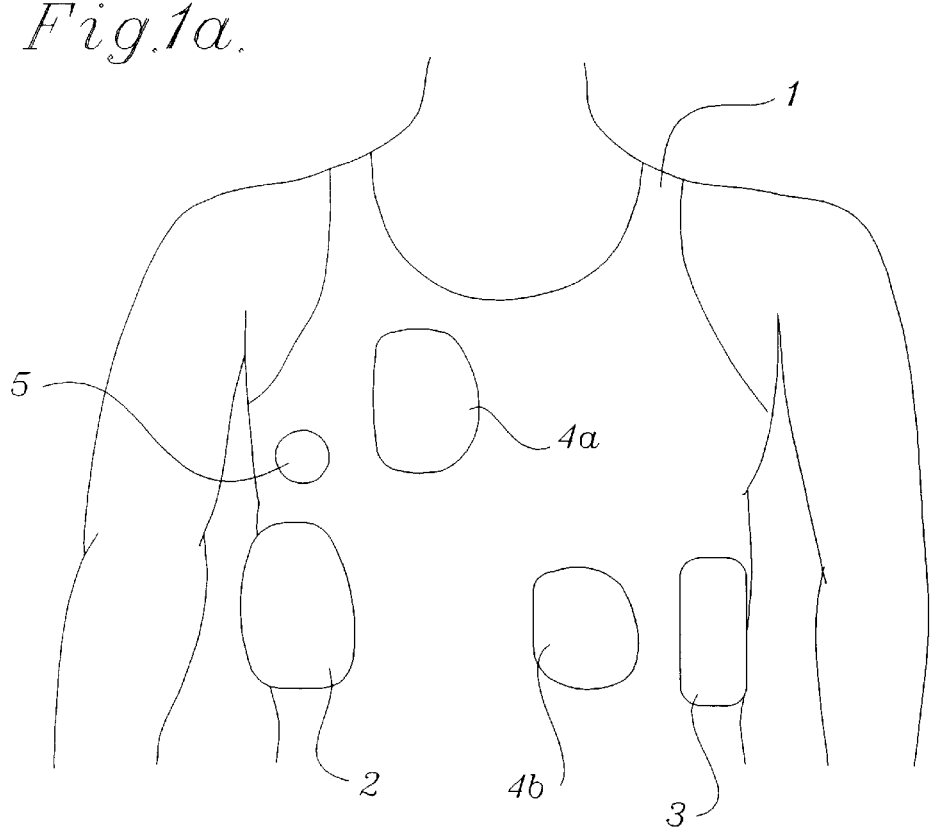
FIG. 1a is a diagrammatic elevational view of a sensing device worn as part of a treatment vest.

While the invention may be embodied in any type of patient care device, including monitoring, or monitoring and treatment of the patient, it is readily adaptable to be used in a patient-worn device. It is, however, contemplated that the invention could be utilized in apparatus that is not attached to the patient and in which signals derived from the patient are communicated to a nonpatient-worn apparatus. FIG. 1a shows an embodiment in which a patient-worn device is utilized. Such a patient-worn harness or vest that provides for both sensing and automatic treatment is described in U.S. Pat. No. 4,928,690 which is incorporated by reference herein.

FIG. 1a shows patient wearing a harness or vest 1, which can incorporate sensors for detecting cardiac function, treatment electrodes, and the control to operate both sensing, patient monitoring, treatment and other patient desired activities. The embodiment in FIG. 1a shows a control 2 which can utilize logic control such as a microprocessor to operate either the sensing/monitoring function or the treatment function or both. With some systems it may be desirable to have separate controls involved with monitoring and treatment. A power supply such as battery pack 3 can be used to power the unit for both the monitoring and the treatment modes. A sensing electrode 5 is positioned adjacent to the patient so as to permit monitoring of cardiac function. It will be understood that in most of the embodiments more than one monitoring sensor will be utilized. In addition, in some embodiments some of the sensors may be combined with electrodes that deliver therapeutic shock treatment. As shown in FIG. 1a, treatment electrodes 4a and 4b are utilized, and the sensor 5 for cardiac function monitoring is a separate unit.

Figure 1B:
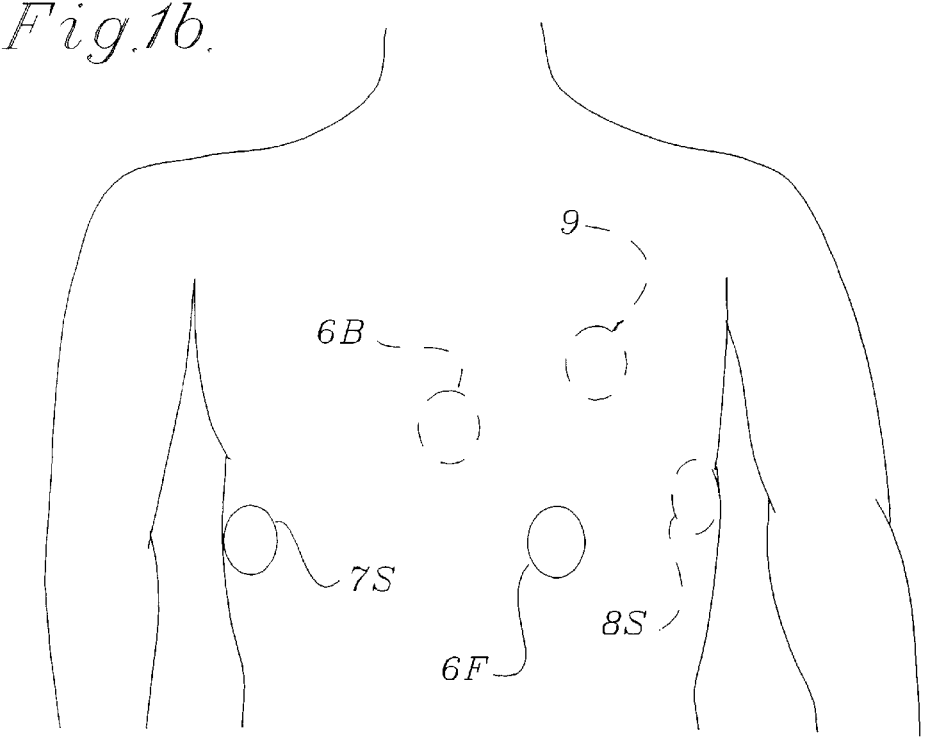
FIG. 1b is a diagrammatic of a body showing sensing electrode placement in a presently preferred embodiment.

In one presently preferred embodiment four sensors are utilized to monitor the patient cardiac condition. FIG. 1b shows their position on the patient. It is understood that while FIG. 1a shows the utilization of a vest or harness to affix sensor 5, other means of placing the sensor adjacent to the patient so that a signal may be detected can also be utilized. A harness or undergarment considerably briefer than the vest shown in FIG. 1a is contemplated. It would also be possible to utilize the invention by attaching the electrodes to the patient in a conventional manner. FIG. 1b shows a front sensor 6f and a back sensor 6b positioned generally medially on the patient. The position of the sensors will be placed in a manner so that they are generally diametrically opposite each other about the patient, however, as shown they can be positioned slightly off the center of the patient to avoid the back sensor 6b from interfering or causing discomfort with the patient's spine. This set of sensors will normally be used to derive a signal which will be referred to as FB meaning front-to-back. A second set of sensors are shown in the pair of 8s and 7s.

Similarly, these two sensors are positioned on the lateral "sides" of the patient and are generally diametrically opposite of each other. It is desirable that the front-to-back (FB) sensor pair, 6f and 6b, be positioned approximately 90 degrees from the side to side (SS) of sensors 7s and 8s. As such the diameter connecting the front-to-back sensors would generally be perpendicular to the diameter connecting the side-to-side pair of sensors. As shown, sensor pair 6f and 6b are slightly offset from the medial line of the patient, and therefore sensors 7s and 8s have also been rotated slightly. In this manner sensor 7s is slightly on the front of the patient's chest while sensor 8s is slightly toward the patient's back, to try to maintain the general relationship of 90 degrees phase between the respective pairs of sensors. Practice, comfort of the patient and security of the sensors may dictate their specific placement while only generally trying to adhere to the 90 degrees phase relationship. Other sensor positions will be apparent to those skilled in the medical care field upon viewing the invention. Similarly, as shown in FIG. 1b, the sensors are applied in the plane of the heart, while utilizing the invention in other patient situations it may be desirable or necessary to position its sensors in different planes.

Sensors 6–9 may be of any acceptable type that can be utilized for typical ECG application. The sensors pick up the analog QRS waveform from the patient's body and pass the signal to receiving circuitry in control 2 for digitization and processing.

Also shown in FIG. 1b is a ground driven electrode 9. The ground driven electrode 9 can be used to reduce the effects of noise and detect if a sensor has fallen off or become disconnected from the patient circuit. A frequency signal, higher than the frequency normally seen in the ECG waveform, is driven into the body via the ground sensor 9. The higher frequency signal can be detected on one of the sensors 6, 7 and 8. The detected signal is an indication that the respective sensors 6, 7 and 8 are contacting the skin. The failure of a higher frequency signal from the ground driven electrode 9 to be detected at the four sensors 6B, 6F, 7 and 8 can be used as an indication of a "fall-off." The control can utilize the intelligence of having detected a fall-off to assign an appropriate level of credibility to signals derived from or failing to be received from electrodes which have been indicated as having fallen off due to a failure to detect the higher frequency from the driven ground electrode.

Figure 2A:
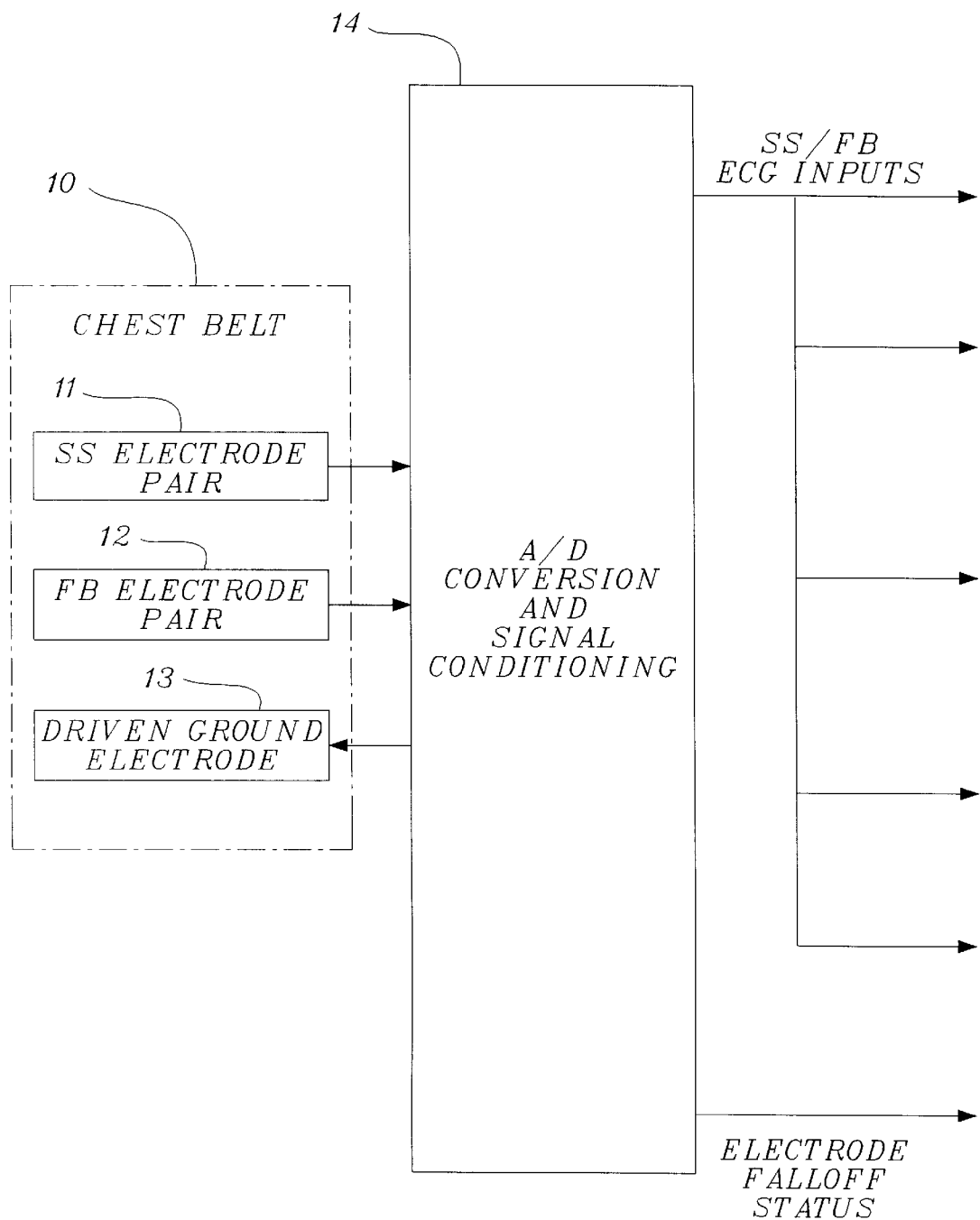
FIGS. 2a–2c are diagrammatics of an arrhythmia detection system.
Figure 2B:
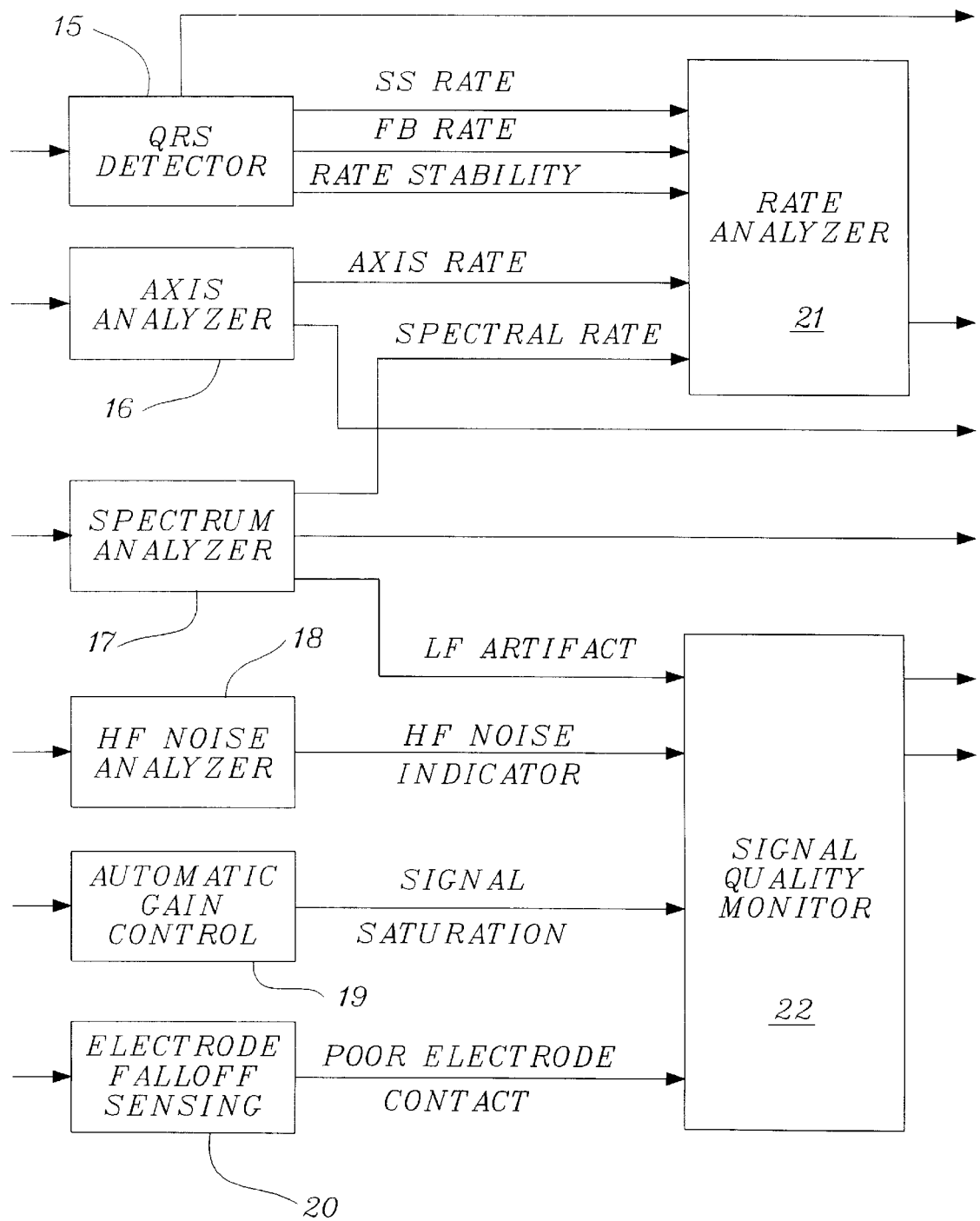
Figure 2C:
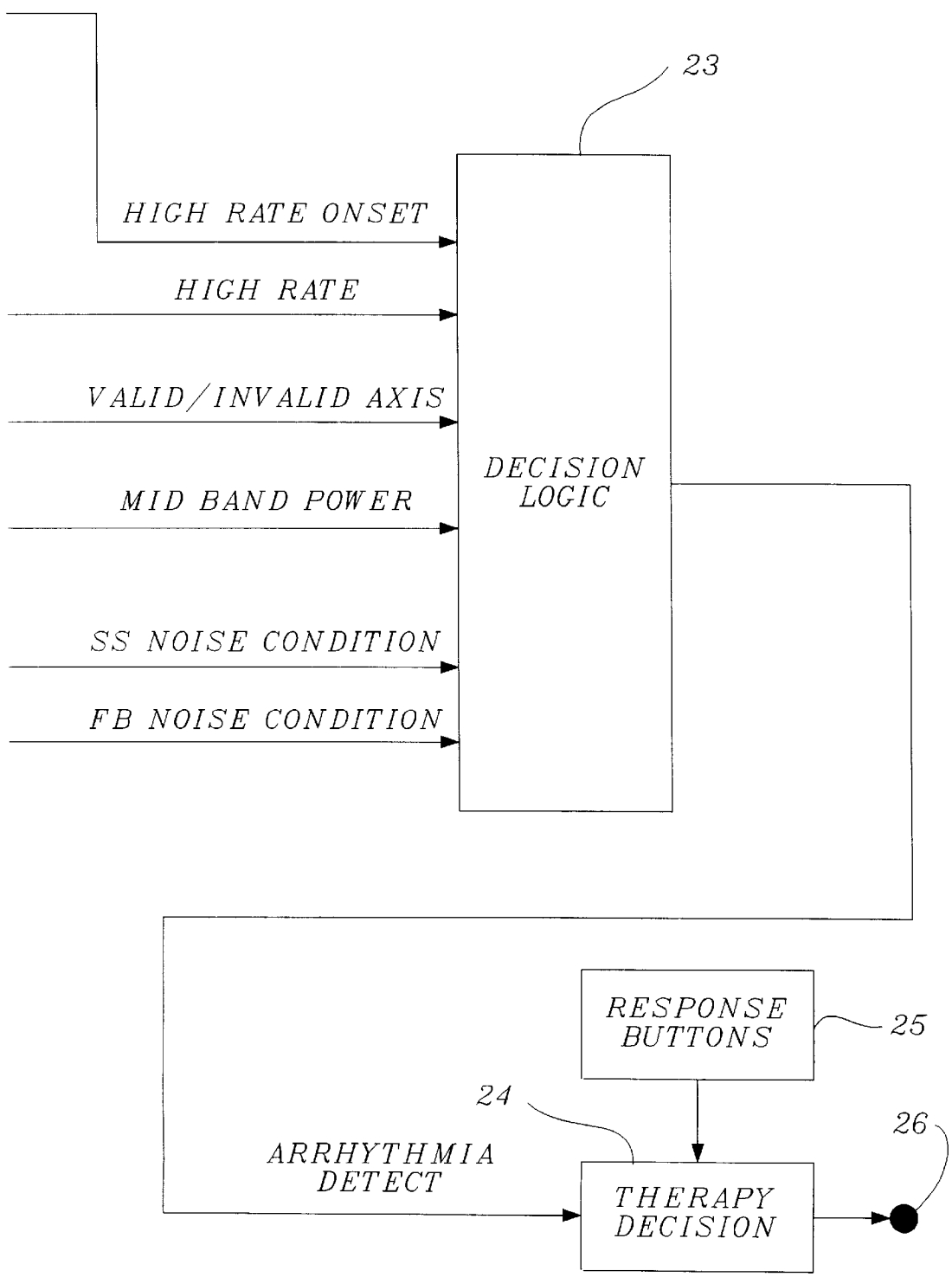

FIGS. 2a–2c show a system block diagram for an arrhythmia detection system. The inputs to the system generally come from a series of sensors which may in this embodiment be located on a chest belt 10. As previously discussed, the sensors are located to be generally orthogonal. While this embodiment uses a chest belt, a vest or other type of attachment can also be utilized. A side-to-side pair of electrodes 11 are contained in the chest belt. These may be of a type as previously described with regard to FIG. 1b as sensors SS 7 and 8. Similarly, a front-to-back electrode pair 12 is contained in the chest belt, and these may be sensors 6b and 6f as shown in FIG. 1b. Also contained in the chest belt is a driven ground electrode 13 used to provide fall-off detection and a signal ground reference. This driven ground electrode 13 may be located in any convenient position, it may be located in the back of a patient as shown in FIG. 1b as ground electrode 9.

The signals derived from the sensors/electrodes in belt 10 are fed to an analog to digital conversion and signal conditioning block 14. Block 14 can utilize conventional signal generators for driving the driven ground electrode 13, and A to D converters for digitizing the inputs from the electrode sensors 11 and 12. Digital signals corresponding to the front-to-back and side-to-side electrodes are sent from the converter 14 to an electrode fall-off sensing unit 20. Failure to detect the higher frequency of the fall-off electrode in the respective side-to-side and front-to-back electrode signals can indicate that one or more respective electrodes have lost contact. Electrode fall-off sensing unit 20 outputs a poor electrode contact signal to a signal quality monitor 22.

Similarly, side-to-side and front-to-back ECG inputs that have been digitized are sent to an automatic gain control unit 19 and a high frequency noise analyzer 18. Based on the respective signal characteristics, the analyzer and gain controls 18 and 19 produce output signals representing signal quality to the signal quality monitor 22. Signal quality monitor 22 provides a signal to the cardiac function decision logic 23 which is indicative of the credibility to be given to the side-to-side contact related conditions and the front-to-back contact related conditions.

While the sensing shown and discussed uses four electrodes, an FB pair and a SS pair, it is understood that other configurations can be used. Two pairs of electrodes can be used and placed in positions other than FB or SS, as long as the sensors can detect or indicate phase changes in the cardiac signal. In some embodiments less than four electrodes may be utilized where the electrode positions and output signals can be utilized to detect or indicate a phase change. Some applications may utilize 3, 5, 6 or other numbers of sensors as appropriate to the circumstance.

The decision logic for cardiac function decision logic block 23 evaluates the inputs it receives to determine the patient's cardiac condition. An arrhythmia detection decision is presented to therapy decision block 24. The therapy decision can be delayed by a conscious patient by activation of the response buttons 25. The cardiac monitor can be used in conjunction with a treatment unit such as a defibrillator to provide electric shock therapy. The output of the decision logic can become vital therefore redundant analysis is built into the system so as to minimize the failure to diagnose a treatable condition while avoiding the administering of treatment in a counter-indicated condition.

In the embodiment shown in FIGS. 2a–2c show three separate analyses are used as inputs to the decision logic 23. The first analysis is made using a QRS detector, 15, which utilizes the respective ECG signals of the side-to-side (SS) and front-to-back (FB) electrodes to calculate rates. In addition, the QRS detector 15 determines a rate stability based upon the change in the respective ECG heart rate changes. Signals indicative of these values are fed to a rate analyzer 21.

A second analysis is utilized determining the electrical axis of the patient heart using vector cardiographic techniques. The axis analyzer 16 provides output signals indicative of a rate to the rate analyzer 21. In addition, the axis analyzer 16 determines the vector of the electrical axis of the heart and can output a valid/invalid signal indication if the axis of the heart indicates a treatable/non-treatable condition. The information is passed to the decision logic 23 for evaluation in determining the treatment or other utilization of patient condition.

A third analysis is performed on the side-to-side and front-to-back ECG inputs utilizing a spectrum analyzer 17. A spectrum analyzer may use fast Fourier transform, or other techniques, to measure and evaluate the respective SS and FB ECG input signal frequency components. The spectrum analyzer also processes a spectral rate which is fed to the rate analyzer 21. The rate analyzer 21 has a number of inputs available to it. In addition, the spectrum analyzer 17 provides spectral component amplitude information to the logic decision block 23. The presence of certain spectral components can be indicative of certain cardiac functions. In addition, a low frequency (LF) artifact indication can be fed to the signal quality monitor 22 from the spectrum analyzer 17. The low frequency artifact signal (LF) can be indicative of low frequency noise in the system or baseline wandering.

As can be seen, the rate analyzer 21 has a number of rate inputs which have been derived from various outputs of the three analyzers, 15, 16 and 17. The rate analyzer can view each of these rates separately and determine the signal which is most indicative of the patient condition. Rate analyzer 21 may initially look to the QRS detector rates SS and FB. If these rates are equal it may assume that this is the proper rate. However, if the rate stability signal begins to change or if the front-to-back or side-to-side rates begin to differ, it can use the axis rate or spectral rate to determine the proper heart rate. The rate analyzer can track the stability of the axis rate and the spectral rate to value the reliability of those respective signals. At any time it can use multiple inputs to determine the best rate to indicate the patient condition. In addition, the rate analyzer can reevaluate the rate inputs individually and independently or in comparison to one another. If it determines that the best available rate signal indicates a high rate, it can then output to the logic decision 23 that a high rate has been detected. Similarly, the inputs to the decision logic can be continuously reviewed to determine if the patient is having a treatable event. The decision logic 23 can then indicate to the therapy decision block 24 that it has detected a treatable condition. Depending upon the specific patient characteristics, a treatment may be initiated based upon the output 26 of the therapy decision mechanism. In some embodiments there may be intervening patient parameters such as a turnoff button or a tactile signaling device which can be also implemented. Response buttons 25 and tactile signaling device are located on the wearable device so that if a condition is sensed, a signal to the patient announces the potential treatment. The patient can then press button 25 to indicate his consciousness which can be used in the evaluation means and detection algorithm to influence or withhold treatment. The decision logic would normally update its output periodically whereas some embodiments would only output after a treatable condition has been determined to exist for a given period of time.

Figure 3B:
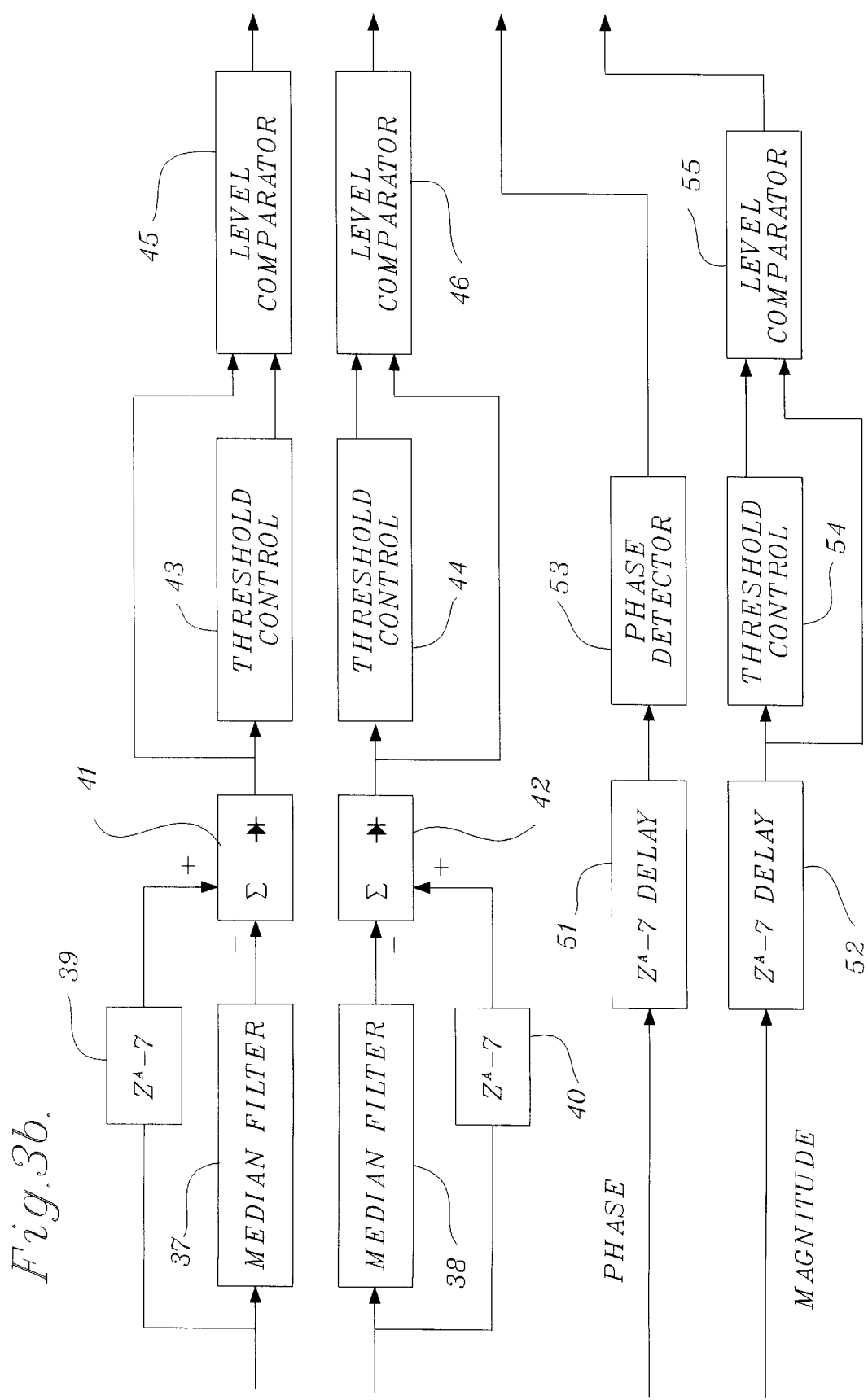
Figure 3C:
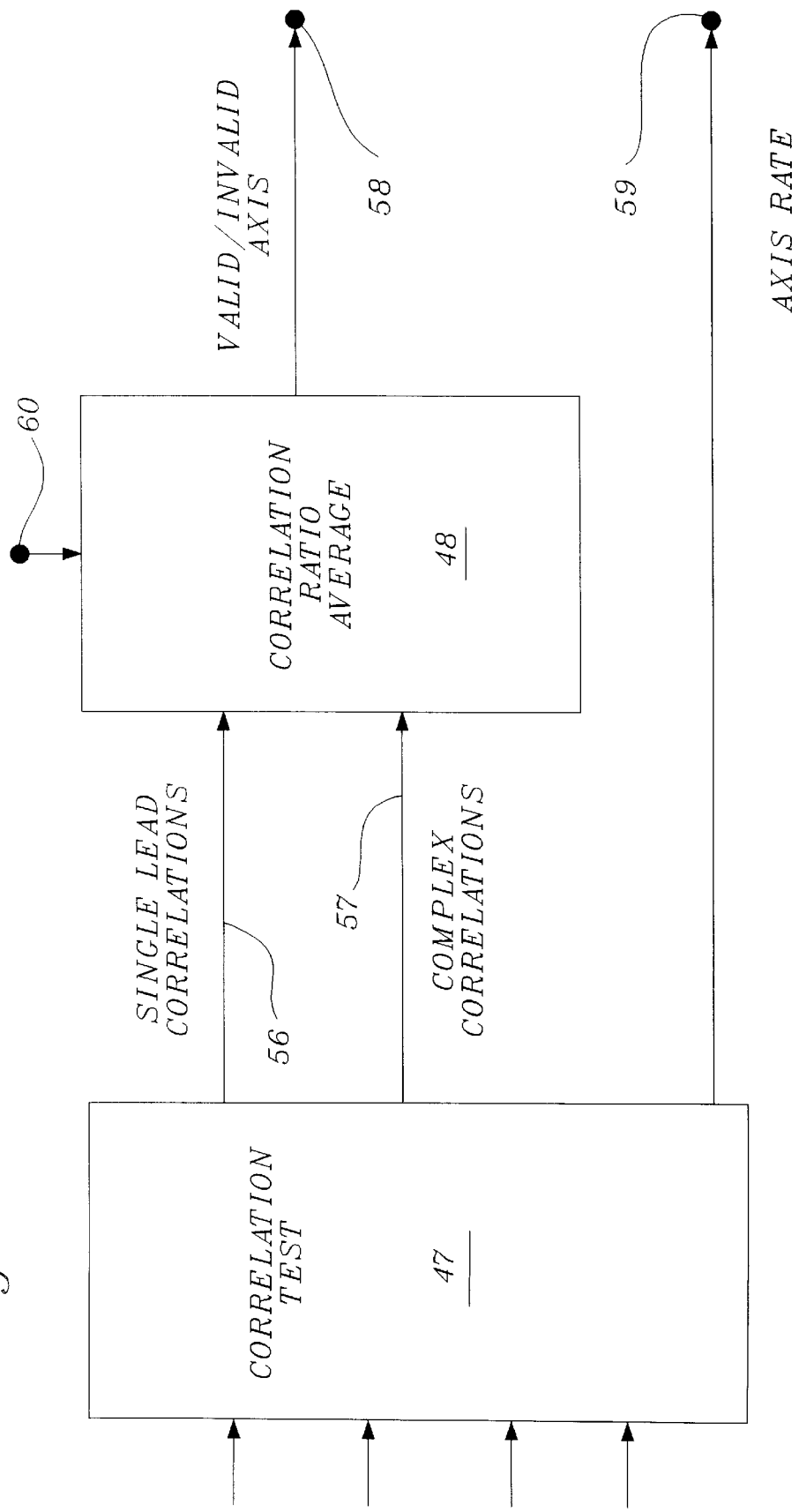

Referring to FIGS. 3a–3c, there are shown a diagrammatics of an axis analyzer/detector. This block diagram is similar to the apparatus as described in FIG. 2b at reference 16. This is one embodiment of the axis analyzer that can be used in practicing this invention. In the axis analyzer/detector the SS and FB ECG input signals, 31 and 32, are fed into band pass filters 33 and 34. The axis analyzer/detector is used to perform a vector cardiography analysis where the signal will be examined to provide a reference indicative of the plane of the electrical axis of the heart being monitored. A treatable condition is highly probable when an unexplainable shift in the electrical axis is detected. The analyzer/detector monitors the heart axis for a period of time to detect a shift in the vector signals. Band pass filters 33 and 34 are used to eliminate noise and undesired signals which are outside of the passband of interest. The output of the SS band pass filter 33 is fed to the input of a matched filter 35. Similarly the FB band pass filter 34 output is fed to matched filter 36. The numerical coefficients of matched filters 35 and 36 are selected by analysis of the patients normal sinus QRS complex. The SS matched filter 35 coefficients are determined by the normal sinus QRS morphology as seen on the SS ECG input channel. The FB matched filter 36 coefficients are determined by the normal sinus QRS morphology as seen on the FB ECG input channel. The two digitized portions of the signal are formed into a complex signal as shown by 49 and input into the complex matched filter 50. The coefficients utilized in filters 35,36 and 50 are calculated through a baseline procedure that records the normal rhythm and automatically calculates the coefficients of complex matching filters 35,36 and 50 when the system is first placed on the patient and the patient is known to be in a normal sinus rhythm.

Delay processing blocks 51 and 52 delay their respective input signals by seven sample periods. The delay is necessary to allow outputs of processing blocks 45, 46. 53 and 55 to be in time sync. The phase output component of the complex matched filter 50, after being delayed by 51, is fed to a phase detector 53. The phase detector continuously monitors the phase component for zero crossing conditions and, when detected, signals correlation test block 47. The magnitude output of complex matched filter 50, after delay 52, is fed into threshold control block 54 and level comparator 55. Threshold control block 54 automatically calculates the appropriate threshold to be used by level comparator 55 based on the past history of the input signal. Since signal amplitudes may vary according to the quality of signal correlation's occurring in the complex matched filter 50, the threshold level used is permitted to vary within a preset or programmable range of values and typically will be set to less than 90% of previously detected peak levels. Adjustment of the threshold values can be used to control the sensitivity of the axis detector. Level comparator 55 compares the magnitude component to the threshold value and indicates to correlation test block 47 when the magnitude component is above the threshold value. Correlation test block 47 examines the timing relationship of the output of phase detector 53 and level comparator 55. If the patients normal sinus rhythm is being processed by the axis detector, and the matched filter coefficients are properly matched to the signal, the level comparator should show that the magnitude component is above the threshold value at the same point in time when the phase detector 53 indicates a zero crossing has occurred.

The occurrence of a single magnitude peak at a given instant of time, that does not have a corresponding zero phase crossing point, may not be significant compared to a phase shift away from the magnitude peaks that is maintained over a period of time or an erratically shifting phase variation. An output 57 is used by correlation ratio average block 48 to indicate the probability of a treatable condition.

Figure 4A:
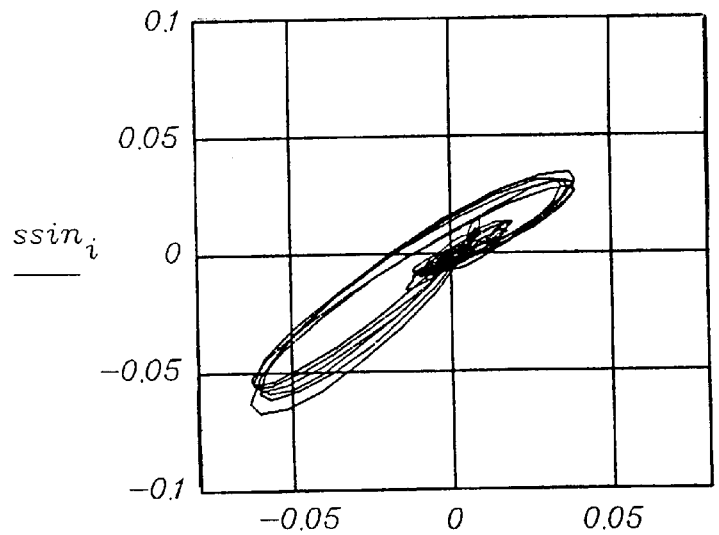
FIGS. 4a–d are wave forms from an axis analyzer/detector such as shown in FIGS. 3a–3c.
Figure 4B:
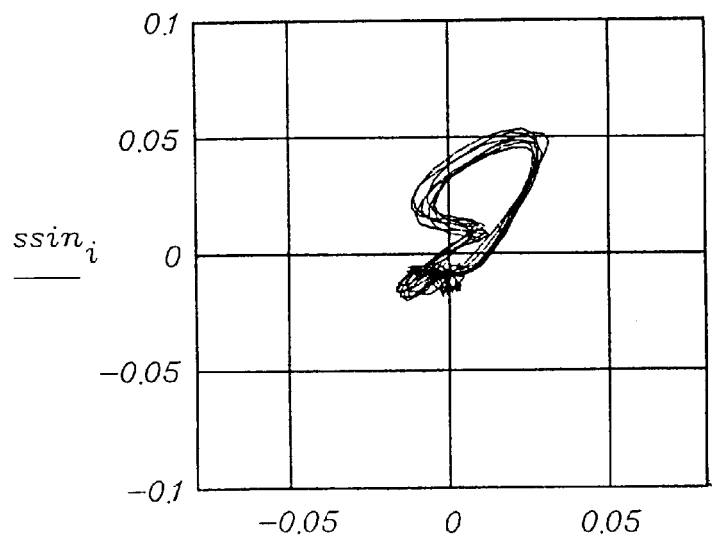
Figure 4C:
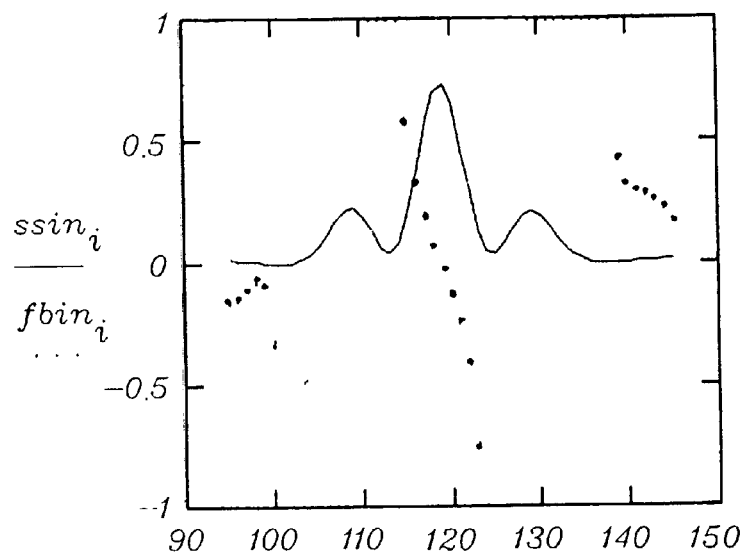
Figure 4D:
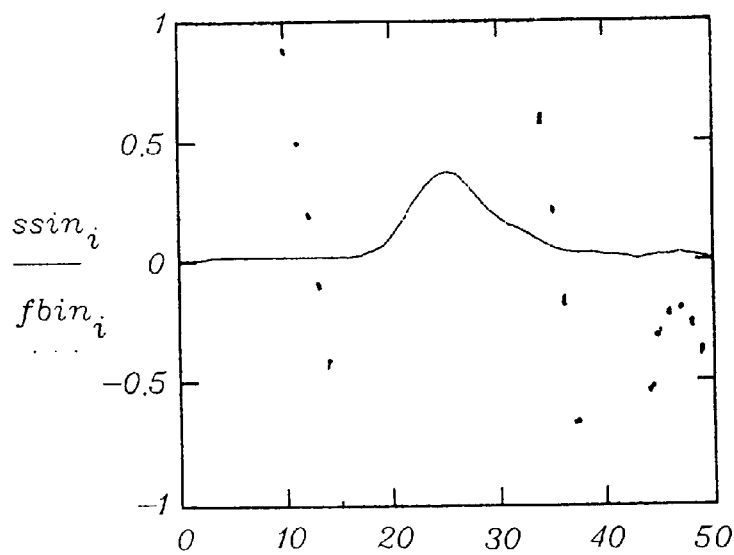

The input to the complex matching filter in a normal condition is shown in FIG. 4a. The output is shown in FIG. 4c for a normal condition. FIGS. 4b and 4d show respectively the input and output during a detected phase shift condition. FIG. 4c with a normal rhythm shows there is established a range of the peak magnitude and a defined zero phase crossing area. On FIG. 4c the phase crossing is shown as dots, while the curve shows the magnitude. FIG. 4c shows that the phase crossing points as dots or points, corresponding generally within the range of the peak magnitude.

When an arrhythmia occurs such as shown in FIG. 4b, the phase crossing points shown in FIG. 4d are shifted out of the range of the peak magnitude. In a supraventricular tachycardia, one that is originating in the atrium and not in the ventricle, the ventricular response is not greatly affected although the heart rate may increase. Therefore, a radical shift between the phase zero crossing does not occur. Utilizing this characteristic, it is possible to discriminate between supraventricular tachycardias versus ventricular tachycardias or ventricular fibrillation. Complex matching filter 50 can include an IIR filter, or infinite impulse response filter. The analyzer may also use an FIR filter, finite impulse response filter. Both of these filter types are well-known in digital signal processing and, in fact, in some embodiments may be implemented by a digital signal processor, DSP, unit. It will generally be desirable to use a finite impulse response filter to realize a linear phase response.

Correlation ratio average block 48 makes use of two inputs, single lead correlations 56 and complex correlations 57, to derive the valid/invalid axis output 58. A single lead correlation processor is included for both the SS and FB input channels. Processing blocks 35,37,39,41,43 and 45 make up the SS single lead correlation channel while processing blocks 36,38,40,42,44 and 46 make up the FB single lead correlation channel. Both SS and FB processing channels contain identical signal processing algorithms and the SS channel will be referenced by this discussion.

The output from band pass filter 33 is fed to SS matched filter 35. The output amplitude of matched filter 35 is directly related to the quality of signal correlation occurring on the SS channel. Since the coefficients of matched filter 35 are selected based on the patient's normal sinus QRS morphology, the output amplitude will be maximum when the patient's normal sinus rhythm is passed through the filter. A large amplitude output peak will occur for every QRS complex processed by the matched filter. The output of the matched filter section is fed to a median filter network consisting of processing blocks 37, 39 and 41. The purpose of the median filter 37 and summation/rectification network 41 is to allow short duration correlation peaks to pass through the system unaltered. Long duration signals resulting from matched filter correlation's with QRS T waves or amplitude offsets at the output of the matched filter will be removed. The summation/rectification block 41 incorporates a half wave rectification step which results in an output containing values which are only greater than or equal to zero. The output from summation and rectification block 41 is fed to threshold control block 43 and to level comparator 45. Threshold control block 43 automatically calculates the appropriate threshold to be used by level comparator 45 based on the past history of the input signal. Since signal amplitudes may vary according to the quality of signal correlation's occurring in matched filter 35, the threshold level used is permitted to vary within a preset or programmable range of values and typically will be set to less than 90% of previously detected peak levels. Adjustment of the threshold values can be used to control the sensitivity of the single lead correlation detection channel and ultimately the axis detector itself. Level comparator 45 compares the magnitude output of the summation/rectification block 41 to the threshold value and indicates to correlation test block 47 when the signal level is above the threshold value.

Figure 5A:
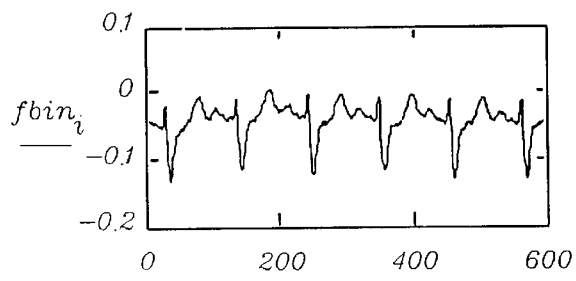
FIGS. 5a–e are wave forms from an axis analyzer/detector such as shown in FIGS. 3a–3c.
Figure 5B:
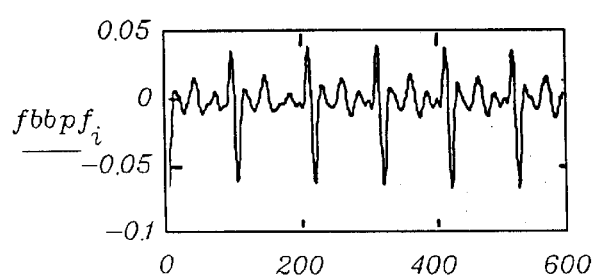
Figure 5C:
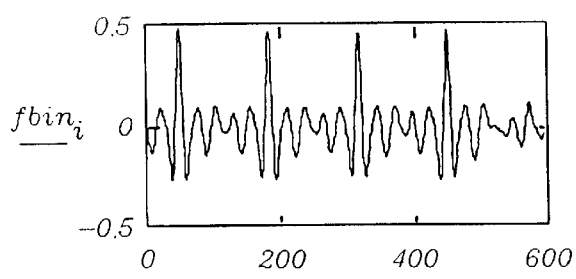
Figure 5D:
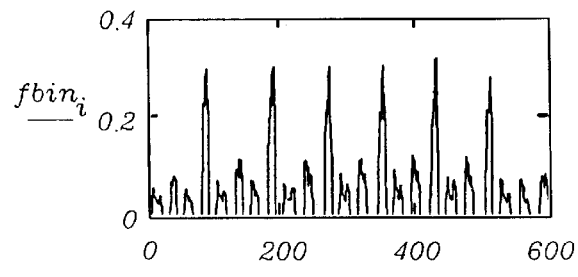
Figure 5E:
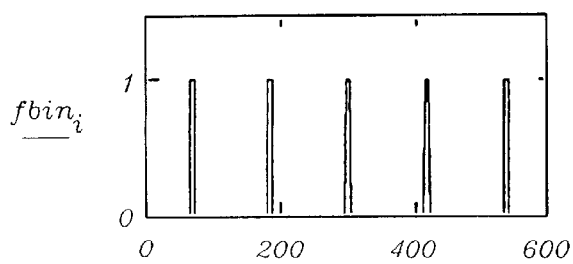

Waveform diagrams shown in FIGS. 5A through 5E demonstrate signals obtained throughout the single lead correlation channels under conditions where the patients normal sinus rhythm is being processed. FIG. 5A and 5B show the raw input SS ECG signal 31 and output of band pass filter 33. FIG. 5C demonstrates the amplitude peaks which occur as a result of con-elation of the QRS complex with the matched filter impulse response. FIG. 5D shows the signal levels which are presented to level comparator 45. FIG. 5E represents the signal fed to correlation test block 47 for both the SS and FB channels. Since each channel is matched to the morphology of the input waveforms the signal inputs to correlation test block 47 should be in time sync. In addition, due to delay blocks 51 and 52 in the complex matched filter channel, the complex magnitude and phase outputs, 55 and 53, will also be in time sync. When an arrhythmia occurs, specifically some forms of ventricular tachycardia, the single lead correlation channels will continue to provide an output due to the large signal amplitude resulting from the ventricular depolarization cycle. Since the channel is not matched to this morphology the amplitude output of matched filter block 35 may not be as large as when processing normal sinus rhythm but will be large enough to overcome the threshold limitation posed by threshold control block 43. In this case single lead correlation information is presented to correlation test block 47 but complex lead correlation's will be absent.

Correlation test block 47 outputs single lead correlation information 56 and complex correlation information 57 to correlation ratio average processing block 48. The correlation ratio processing block 48 determines the ratio of single lead to complex lead correlation's over a preset or programmable time window which can be generally set to less than ten seconds. When the calculated correlation ratio average exceeds a preset or programmable threshold 60, an invalid axis condition is indicated. Threshold values for the correlation average arc typically set between a value of greater than one and less than 100. Low threshold settings will result in increased detection sensitivity. Output 58 provides a status to the system which indicates a valid or invalid axis condition. In addition, since magnitude peaks are available from both the single (FIG. 5E) and complex (FIG. 4C) correlation channels the correlation test block c:an determine the patient's heart rate and provide an additional heart rate output 59.

During operation when the system is processing the patient's normal sinus rhythm, the number of single lead correlation's should be consistent with the number of complex lead correlation's. The ratio of single lead to complex lead correlation's over a period of time should remain close to one. If a ventricular arrhythmia occurs which results in an axis shift the number of single lead correlation's will become larger than complex lead correlation's due to the resulting phase shift. In this case the ratio will become large and care must be taken to prevent the algorithm from performing a division by zero operation. It is normal to expect that periodic zero crossings corresponding to magnitude peaks will occur during certain conditions. It becomes necessary to examine the average of the single to complex correlation's over time to determine the axis shift condition.

Figure 6B:
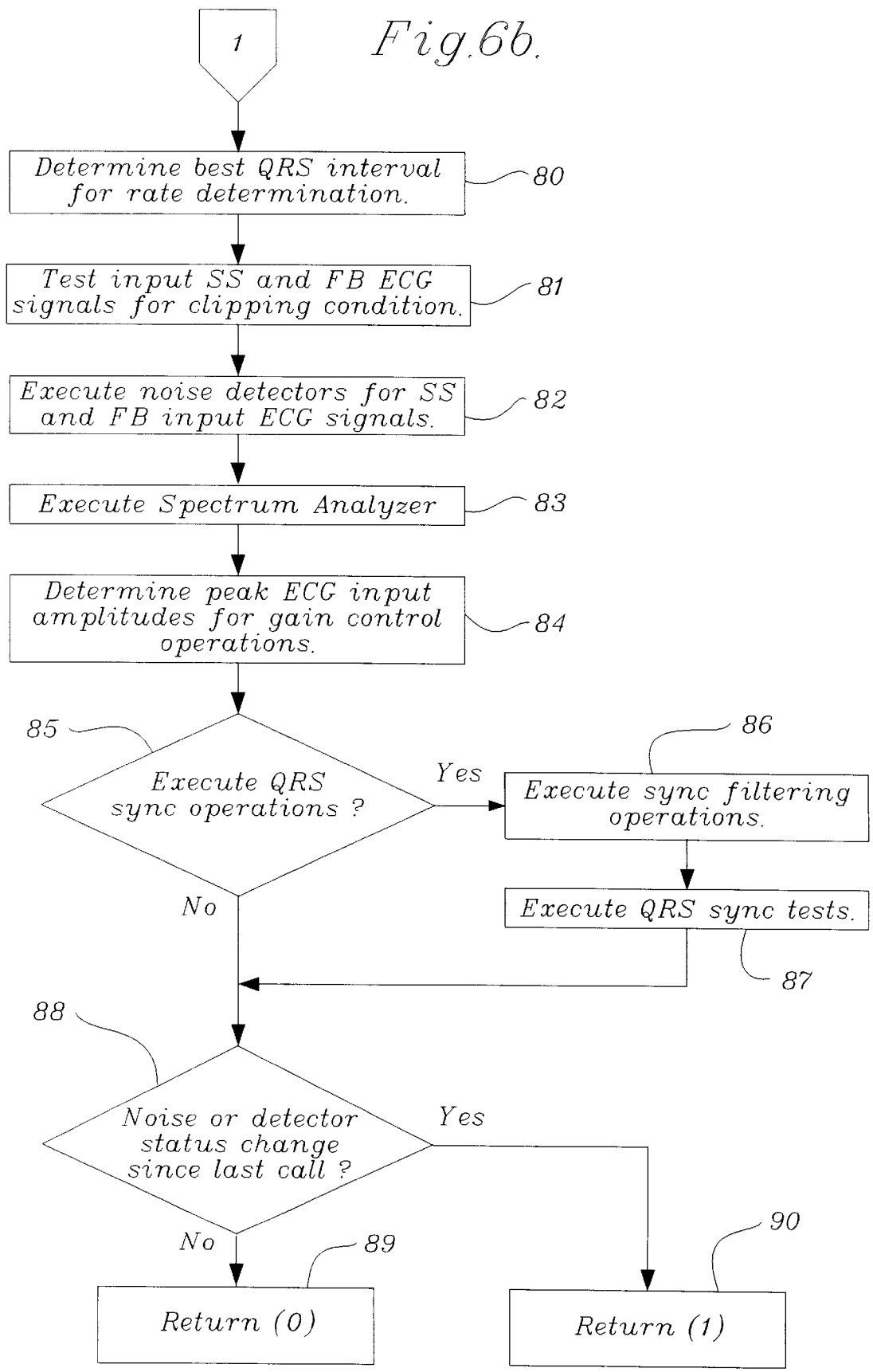

Referring to FIGS. 6a and 6b, there is shown a program flowchart for an arrhythmia detection apparatus utilizing the invention. It is understood that other apparatus and architecture can be utilized to implement the invention. A preferred embodiment of the invention is to use digital signal processing techniques and specifically to use a digital signal processor, DSP, to perform filtering and decision operations associated with the detection algorithm. The processing shown in FIGS. 6a and 6b can be executed at the system sampling rate, under interrupt control, to implement the detection functions. As an example, if a sampling rate of 200 Hz were used, the interrupt service routine diagrammed in FIG. 6b would be executed 200 times per second of operation. Routines external to the interrupt service could monitor the state of the axis detector, rate detectors and spectrum analyzer to determine the patient's condition in real time.

Reference blocks 70 through 90 are used in FIGS. 6a and 6b to describe the methodology in implementing the system on a digital system processor. With the sensors installed, the detection procedure is begun by initiation of a sampling sequence with a fixed sampling period, 70 with the sensor inputs being stored in the appropriate DSP memory. As the sensors are periodically read, the threshold timer is updated and the DSP is set up 71 to process incoming data samples from the sensors. Band pass filtering operations are performed 72 for the axis and rate detectors. Next, the axis detector matched filter processing operations are performed 73. Then the QRS detector filtering operations are executed at 74 and the QRS detection threshold operations for the side-to-side and front-to-back back ECG signals are performed at 75. Matched filter threshold operations are performed for the side-to-side and front-to-back ECG sensors 76.

The DSP performs the complex matched filter threshold operations at 77. Next the QRS detectors for the side-to-side and front-to-back ECG input signals are executed 78. Rate detector stability tests are performed 79 to determine the stability of detected SS and FB rates. The best QRS interval for rate determination is set 80. Processing steps continue to determine if a noise condition exists. The input sensor signals for the side-to-side and front-to-back ECG signals are tested for clipping conditions, 81. The DSP then executes operations to detect noise for the side-to-side and front-to-back ECG input signals, 82.

Spectrum analyzer functions are executed, 83, to determine the input signal frequency content. Peak ECG input amplitudes for gain control operations are determined at 84. The DSP unit determines if QRS synchronization functions are required, 85, and if the result is positive, the DSP executes a synchronizing filtering operation 86 and a subsequent QRS synchronization test 87. Synchronization signals may be used by therapy routines to synchronize the output therapy pulse to the input ECG signal "R" wave.

If the output from 85 is negative, the DSP checks to see if a noise or detector status change has occurred since the last processing cycle, 88. If no change has occurred in the noise or detector status, the DSP executes 89 a return (0). If the noise or detector status has changed since the last call the DSP executes 90, a return (1). Noise and detector status flags can be examined by software functions external to the interrupt processing routines to determine the presence of noise or arrhythmia conditions.

In general, if the rate detection system indicates that the rate is above a preset or programmable threshold and the axis detector indicates an abnormal condition, an arrhythmia is declared. The rate threshold is generally programmable between the range of 100 and 200 beats per minute. Combinations of outputs from the spectrum analyzer and rate detectors can also trigger arrhythmia declarations under certain circumstances such as when the system is operating in a single lead detection mode. Single lead detection mode may occur if noise contamination is present on one of the two leads, either SS or FB. In this case, since the axis detector requires two input leads, an arrhythmia declaration may occur based on the rate and spectral content of the uncontaminated lead.

While certain embodiments and techniques of the invention have been described, it is to be understood that the invention can be practiced in a number of embodiments and methods not shown but consistent with the invention as defined in the attached claims.

I claim:

1. An apparatus for sensing cardiac function in a patient, such apparatus comprising:
    (a) sensors for electrical connection to such patient to sense ECG signals in at least one plane in such patient;

(b) an axis analyzer for deriving a signal representation of the electrical axis of the heart of such patient from said ECG signals;

(c) a detector for detecting changes in said signal representation of the electrical axis of said heart; and (d) evaluation means for determining when said changes in said signal representation indicates a cardiac condition.

2. The apparatus for sensing cardiac function in a patient of claim 1 wherein said sensors include four ECG sensors for electrical connection to such patient.

3. The apparatus for sensing cardiac function in a patient of claim 2 wherein said four sensors are positioned about said patient in pairs and the axis of said pairs are generally perpendicular to each other and generally lie in at least a single plane which passes through the chest cavity of such patient.

4. The apparatus for sensing cardiac function in a patient of claim 3 wherein said sensor pairs include a side-to-side pair and a front-to-back pair.

5. The apparatus for sensing cardiac function in a patient of claim 1 wherein said signal representation includes magnitude and phase components.

6. The apparatus for sensing cardiac function in a patient of claim 5 wherein said phase component includes a zero-cross indication.

7. The apparatus for sensing cardiac function in a patient of claim 6 wherein said evaluation means includes comparing changes in said zero-cross indication.

8. The apparatus for sensing cardiac function in a patient of claim 7 wherein said cardiac condition is determined by comparing the incidence of said zero-cross indication with the period of the peaks of said magnitude component.

9. The apparatus for sensing cardiac function in a patient of claim 8 further comprising:

(a) a harness to be worn by said patient and carrying said sensors; and (b) a QRS detector for detecting at least one rate from said ECG signals;

(c) response buttons used by the patient to signal said evaluation mean of a condition of patient consciousness.

10. The apparatus for sensing cardiac function in a patient of claim 8 further comprising:

a spectrum analyzer receiving said ECG signals.

11. The apparatus for sensing cardiac function in a patient of claim 10 further comprising:

(a) said spectrum analyzer determining a rate;

(b) said axis analyzer determining a rate; and (c) said evaluation means further indicating a cardiac condition from said rate determined by said spectrum analyzer and from said rate from said axis analyzer.

12. The apparatus for sensing cardiac function in a patient of claim 5 wherein said evaluation means includes comparing changes in said magnitude and phase component.

13. The apparatus for sensing cardiac function in a patient of claim 1 further including a QRS detector for detecting at least one rate.

14. The apparatus for sensing cardiac function in a patient of claim 13 further including a rate stability detector for receiving said ECG signals.

15. The apparatus for sensing cardiac function in a patient of claim 13 further including a spectrum analyzer receiving said ECG signals.

16. The apparatus for sensing cardiac function in a patient of claim 1 wherein said axis analyzer also derives a rate signal.

17. The apparatus for sensing cardiac function in a patient of claim 1 further including fall-off sensing.

18. The apparatus for sensing cardiac function in a patient of claim 1 further comprising at least one response button to signal to said evaluation means a condition of patient consciousness.

19. A wearable apparatus for sensing cardiac function in a patient, such apparatus comprising:

(a) sensors for electrical connection to such patient to sense ECG signals;

(b) analyzer for deriving rate information from said ECG signals;

(c) axis analyzer for deriving a signal representation of the electrical axis of the heart of such patient from said ECG signals; and (d) evaluation means for determining cardiac condition from said rate information and said signal representation of the electrical axis of the heart of such patient.

20. The wearable apparatus for sensing cardiac function in a patient of claim 19 wherein said sensors comprise four sensors positioned about said patient in pairs and the axis of said pairs are generally perpendicular planes through the chest cavity of such patient.

21. The wearable apparatus for sensing cardiac function in a patient of claim 19 wherein said signal representation includes magnitude and phase components.

22. The wearable apparatus for sensing cardiac function in a patient of claim 21 wherein said vector component includes a zero-cross indication.

23. The wearable apparatus for sensing cardiac function in a patient of claim 22 wherein said evaluation means includes comparing changes in said zero-cross indication.

24. The wearable apparatus for sensing cardiac function in a patient of claim 23 wherein said cardiac condition is determined by comparing the incidence of said zero-cross indication with the period of the peaks of said magnitude component.

25. The apparatus for sensing cardiac function in a patient of claim 24 further including:

(a) a rate stability detector for receiving said ECG signals; and (b) said evaluation means further uses said rate stability to determine a cardiac condition.

26. The apparatus for sensing cardiac function in a patient of claim 25 further including:

(a) a spectrum analyzer receiving said ECG signals; and (b) said evaluation means further uses the output of said spectrum analyzer to determine cardiac condition.

27. The wearable apparatus for sensing cardiac function of claim 26 wherein:

(a) said axis analyzer further comprises analyzer for deriving other rate information from said signal representation of the electrical axis of the heart of such patient; and (b) said evaluation means further uses said other rate information to determine a cardiac condition.

28. The wearable apparatus for sensing cardiac function of claim 19 wherein:

(a) said axis analyzer further comprises analyzer for deriving other rate information from said signal representation of the electrical axis of the heart of such patient; and (b) said evaluation means further uses said other rate information to determine a cardiac condition.

29. The apparatus for sensing cardiac function in a patient of claim 19 wherein said sensor pairs include a side-to-side pair and a front-to-back pair.

30. A method of sensing cardiac function in a patient comprising:
   (a) electrically connecting sensors to such patient to sense ECG signals in at least one plane;
   (b) deriving from said ECG signals a signal representation of the electrical axis of the heart of such patient;
   (c) detecting changes in said signal representation of the electrical axis of the heart of said patient; and
   (d) determining cardiac condition from said changes in the electrical axis of the heart of said patient.

31. The method of sensing cardiac function in a patient of claim 30 wherein said deriving a signal representation of the electrical axis of the heart of such patient further includes deriving said signal representation with magnitude and phase components.

32. The method of sensing cardiac function in a patient of claim 31 wherein said vector component includes a zero-cross indication.

33. The method of sensing cardiac function in a patient of claim 32 further including deriving a rate signal from said signal representation of the electrical axis of such heart.

34. The method of sensing cardiac function in a patient of claim 33 wherein said determining cardiac condition further comprises comparing the incidence of said zero-cross indication with the period of the peaks of said magnitude component.

35. The method of sensing cardiac function in a patient of claim 34 further comprising detecting cardiac condition after a change in the signal representation of the electrical axis of said heart by the lack of co-incidence of said peak magnitude and said zero-cross indication.

36. The method of sensing cardiac function in a patient of claim 35 further comprising connecting said sensors to an ambulatory patient by mounting said sensors in a harness wearable by said patient.

* * * * *